(12) United States Patent
Nakamura et al.

(10) Patent No.: US 12,387,826 B2
(45) Date of Patent: Aug. 12, 2025

(54) DOCUMENT CREATION APPARATUS, DOCUMENT CREATION METHOD, AND DOCUMENT CREATION PROGRAM FOR CREATING DOCUMENT BASED ON MEDICAL IMAGE

(71) Applicant: FUJIFILM Corporation, Tokyo (JP)

(72) Inventors: Keigo Nakamura, Tokyo (JP); Yuya Hamaguchi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 94 days.

(21) Appl. No.: 18/460,583

(22) Filed: Sep. 3, 2023

(65) Prior Publication Data

US 2023/0420096 A1 Dec. 28, 2023

Related U.S. Application Data

(63) Continuation of application No. PCT/JP2022/002462, filed on Jan. 24, 2022.

(30) Foreign Application Priority Data

Mar. 19, 2021 (JP) .................................. 2021-046614
Dec. 22, 2021 (JP) .................................. 2021-208719

(51) Int. Cl.
*G06F 40/186* (2020.01)
*G06F 40/40* (2020.01)
(Continued)

(52) U.S. Cl.
CPC ........... *G16H 15/00* (2018.01); *G06F 40/186* (2020.01); *G06F 40/40* (2020.01); *G06T 7/0012* (2013.01)

(58) Field of Classification Search
CPC ........ G16H 30/40; G16H 15/00; G16H 30/20; G06F 18/21; G06F 40/10; G06F 18/2413; G06F 40/56; G06N 20/00; G06N 3/044; G06N 3/08; G06T 7/0016; G06T 2207/20081; G06T 2207/20084; G06T 2200/24; G06T 2207/10072;
(Continued)

(56) References Cited

U.S. PATENT DOCUMENTS

2007/0237377 A1    10/2007  Oosawa
2010/0189366 A1*   7/2010   Iizuka .................... G16H 15/00
                                                    382/209

(Continued)

FOREIGN PATENT DOCUMENTS

JP    2007305107     11/2007
JP    WO2005122002   7/2008

(Continued)

OTHER PUBLICATIONS

WO2005122002A2 (Eng Translation) published on Dec. 22, 2005 by Fujio et al.*

(Continued)

*Primary Examiner* — Rinna Yi
(74) *Attorney, Agent, or Firm* — JCIPRNET

(57) ABSTRACT

A processor acquires criterion information for determining output of a document to be created by using an analysis result including at least one finding for an image, determines, based on the criterion information, output of the document, and outputs at least one document.

9 Claims, 18 Drawing Sheets

(51) Int. Cl.
*G06T 7/00* (2017.01)
*G16H 15/00* (2018.01)

(58) Field of Classification Search
CPC ........ G06T 2207/30064; G06V 10/255; G06V 10/40; G06V 10/751; G06V 10/764; G06V 10/82; G06V 2201/03
See application file for complete search history.

(56) References Cited

U.S. PATENT DOCUMENTS

| | | | |
|---|---|---|---|
| 2016/0314247 | A1* | 10/2016 | Nagao ................... G16H 30/20 |
| 2017/0154156 | A1 | 6/2017 | Sevenster et al. |
| 2018/0286503 | A1 | 10/2018 | Sevenster |
| 2019/0279751 | A1 | 9/2019 | Nakamura et al. |
| 2021/0035676 | A1 | 2/2021 | Nakamura et al. |

FOREIGN PATENT DOCUMENTS

| | | |
|---|---|---|
| JP | 2012074002 | 4/2012 |
| JP | 2018534029 | 11/2018 |
| JP | 2018537177 | 12/2018 |
| JP | 2019153250 | 9/2019 |
| WO | 2009041586 | 4/2009 |
| WO | 2019208130 | 10/2019 |

OTHER PUBLICATIONS

"Search Report of Europe Counterpart Application", issued on Jul. 19, 2024, p. 1-p. 8.

"International Search Report (Form PCT/ISA/210) of PCT/JP2022/002462", mailed on Apr. 5, 2022, with English translation thereof, pp. 1-7.

"Written Opinion of the International Searching Authority (Form PCT/ISA/237) of PCT/JP2022/002462", mailed on Apr. 5, 2022, with English translation thereof, pp. 1-8.

* cited by examiner

FIG. 4

LOCATION OF ABNORMAL SHADOW: UNDER PLEURA OF LEFT LUNG
SIZE OF ABNORMAL SHADOW: 4.2 cm IN DIAMETER
SHAPE OF BOUNDARY: IRREGULAR
ABSORPTION VALUE: SOLID TYPE
SPICULA: +
MASS
PLEURAL CONTACT: +
PLEURAL INDENTATION: +
PLEURAL INFILTRATION: -
CAVITY: -
CALCIFICATION: -

FIG. 5

| NUMBER OF FINDING ITEMS | CREATION METHOD |
| --- | --- |
| 1 | T1 |
| 2 | T2 |
| 3 | T3 |
| 4 | NLP1 |
| 5 | NLP2 |
| 6 OR MORE | NLP1 TO NLP3 |

FIG. 6

| PART AND DISEASE | EVALUATION VALUE |
|---|---|
| A | X1 |
| B | X1 |
| C | X2 |
| D | X3 |
| E | X2 |

FIG. 7

| EVALUATION VALUE | CREATION METHOD |
|---|---|
| X1 | NLP1 |
| X2 | T1 |
| X3 | T2 |
| X4 | T1 + NLP1 |

FIG.15

| PART | DISEASE TYPE | DISEASE NAME | DISEASE FEATURE 1 | DISEASE FEATURE 2 | DISEASE FEATURE 3 | ANATOMICAL LEVEL INFORMATION | SIZE LEVEL INFORMATION | MEDICAL IMAGE INFORMATION | CREATION METHOD |
|---|---|---|---|---|---|---|---|---|---|
| LUNG | NODULAR | LUNG ADENOCARCINOMA | | | | LUNG SEGMENTS (S1 TO S8) | MAJOR AXIS | ☐ ☐ ☐ | <NLP> |
| | DIFFUSE | INTERSTITIAL PNEUMONIA | GROUND GLASS OPACITY | CLINGING TO CHEST WALL | INTERNAL CAVITY | | | ☐ ☐ | <NLP> |
| THORAX/ ABDOMEN | | LYMPH NODE SWELLING | | | | AXILLA, MEDIASTINUM, ABDOMEN | MINOR AXIS | ☐ | <TEMPLATE> |
| LIVER | NODULAR | CYST | LOW ABSORPTION | | | | SMALL | ☐ | <TEMPLATE> |
| | | HEPATOCELLULAR CARCINOMA | Washout | VENOUS PHASE ENHANCEMENT | | | | ☐ ☐ ☐ | <NLP> |
| | DIFFUSE | FATTY LIVER | LOW SIGNAL | | | | | ☐ ☐ | <NLP> |
| | | LIVER CIRRHOSIS | INHOMOGENEOUS | | | | | ☐ ☐ | <TEMPLATE> |
| | OTHERS | POST OPERATION | RIGHT LOBE RESECTION | | | | | ☐ ☐ ☐ | <TEMPLATE> |
| HEAD | NODULAR | GLIOMA | WITH EDEMA | ENHANCED | INDISTINCT MARGIN | | | ☐ ☐ ☐ | <TEMPLATE> |
| | STRUCTURALLY ABNORMAL | DEMENTIA | REDUCED HIPPOCAMPAL VOLUME | | | | | ☐ ☐ ☐ | <TEMPLATE> |

55

DOCUMENT CREATION APPARATUS, DOCUMENT CREATION METHOD, AND DOCUMENT CREATION PROGRAM FOR CREATING DOCUMENT BASED ON MEDICAL IMAGE

CROSS-REFERENCE TO RELATED APPLICATIONS

The present application is a Continuation of PCT International Application No. PCT/JP2022/002462, filed on Jan. 24, 2022, which claims priority to Japanese Patent Application No. 2021-046614, filed on Mar. 19, 2021 and Japanese Patent Application No. 2021-208719, filed on Dec. 22, 2021. Each application above is hereby expressly incorporated by reference, in its entirety, into the present application.

BACKGROUND

Technical Field

The present disclosure relates to a document creation apparatus, a document creation method, and a document creation program.

Related Art

In recent years, advances of medical equipment such as computed tomography (CT) apparatuses and magnetic resonance imaging (MRI) apparatuses have enabled image-based diagnosis using higher-quality high-resolution medical images. In particular, since a region of a lesion can be accurately identified through image-based diagnosis using a CT image, an MRI image, or the like, appropriate treatment has come to be performed based on the identified result.

Additionally, a medical image is analyzed through computer-aided diagnosis (CAD) using a trained model that has been trained using deep learning or the like, and properties such as a shape, a density, a position, and a size of an abnormal shadow of a lesion or the like included in the medical image are detected. The medical image and the analysis result are transmitted to a terminal of a radiologist who interprets the medical image. The radiologist interprets the medical image with reference to the transmitted medical image and analysis result on their interpretation terminal, and creates an interpretation report.

Along with enhancement of the performance of the CT apparatuses and the MRI apparatuses mentioned above, the number of medical images to be interpreted is also increasing. However, the number of radiologists is not enough for the number of medical images. Thus, the radiologists' burden of interpretation work is desirably reduced. Accordingly, various techniques for assisting creation of a medical document such as an interpretation report have been proposed. For example, JPWO2005-122002A1 has proposed a technique of, to standardize terms and abbreviations used in interpretation reports, identifying a template based on input findings and creating a finding remark to be written in an interpretation report from the findings by using the template. WO2019/208130A has also proposed a technique of creating a finding remark including a CAD-based detection result through natural language processing, which is a series of techniques for causing a computer to process a natural language ordinarily used by people by using a neural network such as a recurrent neural network.

Diseases that occur in the human body are diverse, and the number of items and a quantity of text to be written in a finding remark vary from disease to disease. Therefore, to generate a finding remark that can handle all the diseases by using templates, so many types of templates need to be prepared. Additionally, when a finding remark is generated using a neural network, preparation of training data requires lots of labor. Therefore, when a finding remark that can handle all the diseases is generated using a neural network, the cost thereof is enormous. Such an issue occurs not only when documents related to medical images are created but also when documents related to photographic images or the like are created.

SUMMARY OF THE INVENTION

The present disclosure is made in view of the above circumstance, and an object of the present disclosure is to allow a document related to an image to be created with a simple configuration.

A document creation apparatus according to the present disclosure includes at least one processor configured to acquire criterion information for determining output of a document to be created by using an analysis result including at least one finding for an image, and
   determine, based on the criterion information, output of the document, and output at least one document.

Note that in the document creation apparatus according to the present disclosure, the at least one processor may be configured to determine at least one creation method of the document, based on the criterion information,
   create the at least one document by using the at least one creation method that has been determined, and
   output the at least one document that has been created.

Additionally, in the document creation apparatus according to the present disclosure, the at least one processor may be configured to determine the creation method, based on an evaluation result according to the criterion information based on a predetermined evaluation criterion for determining the creation method.

Additionally, in the document creation apparatus according to the present disclosure, the evaluation criterion may include at least one of the number of findings included in the analysis result or the number of pieces of attribute information about the findings.

Additionally, in the document creation apparatus according to the present disclosure, the at least one processor may be configured to determine the creation method with reference to a table in which the criterion information is associated with the creation method according to the criterion information.

Additionally, in the document creation apparatus according to the present disclosure, the at least one processor may be configured to switch a way of determining the creation method in accordance with a predetermined condition.

Additionally, in the document creation apparatus according to the present disclosure, the creation method may be a creation method using a template into which the at least one finding is inserted to create the document.

Additionally, in the document creation apparatus according to the present disclosure, the creation method may be a creation method using natural language processing that uses the at least one finding to create the document.

Additionally, in the document creation apparatus according to the present disclosure, the creation method may be a combination creation method of a creation method using a template into which the at least one finding is inserted to create the document and a creation method using natural language processing that uses the at least one finding to create the document.

Additionally, in the document creation apparatus according to the present disclosure, the at least one processor may be configured to create a plurality of documents, and the plurality of documents may be different in at least one of the finding or the creation method used in creation of the documents.

Additionally, in the document creation apparatus according to the present disclosure, the at least one processor may be configured to display the plurality of documents in a selectable manner.

Additionally, in the document creation apparatus according to the present disclosure, the at least one processor may be configured to display at least one of the creation method or the criterion information of each of the plurality of documents in association with the document.

Additionally, in the document creation apparatus according to the present disclosure, the at least one processor may be configured to receive a correction start instruction for a document designated from among the plurality of documents that are displayed, and
  display, in response to the correction start instruction, another document that is different from the designated document in the creation method, instead of the designated document.

Additionally, in the document creation apparatus according to the present disclosure, the at least one processor may be configured to create a plurality of documents by using the analysis result, and
  determine, based on the criterion information, at least one document to be output from among the plurality of documents.

Additionally, in the document creation apparatus according to the present disclosure, the criterion information may include reliability indicating document appropriateness for the plurality of documents.

Additionally, in the document creation apparatus according to the present disclosure, the at least one processor may be configured to determine at least one document for which the reliability satisfies a criterion, as the document to be output.

Additionally, in the document creation apparatus according to the present disclosure, the at least one processor may be configured to analyze the image to acquire the analysis result.

Additionally, in the document creation apparatus according to the present disclosure, the document may be a finding remark including the analysis result.

Additionally, in the document creation apparatus according to the present disclosure, the document may include a graphical display of the analysis result.

Additionally, in the document creation apparatus according to the present disclosure, the image may be a medical image.

A document creation method according to the present disclosure includes acquiring criterion information for determining output of a document to be created by using an analysis result including at least one finding for an image, and
  determining, based on the criterion information, output of the document, and outputting at least one document.

Note that the document creation method according to the present disclosure may be provided as a program for causing a computer to execute the document creation method.

The present disclosure allows a document related to an image to be created with a simple configuration.

BRIEF DESCRIPTION OF THE DRAWINGS

FIG. 4 is a diagram illustrating an example of findings derived by an image analysis unit;

FIG. 5 is a diagram illustrating an example of a table in which the number of finding items and a document creation method are associated with each other;

FIG. 6 is a diagram illustrating an example of a table in which a part and a disease is associated with an evaluation value;

FIG. 7 is a diagram illustrating an example of a table in which an evaluation value is associated with a document creation method;

FIG. 15 is a diagram illustrating an example of a management database (DB);

DETAILED DESCRIPTION

Embodiments of the present disclosure will be described below with reference to the drawings. A configuration of a medical information system to which a document creation apparatus according to a first embodiment is applied will be described first.

Figure 1:
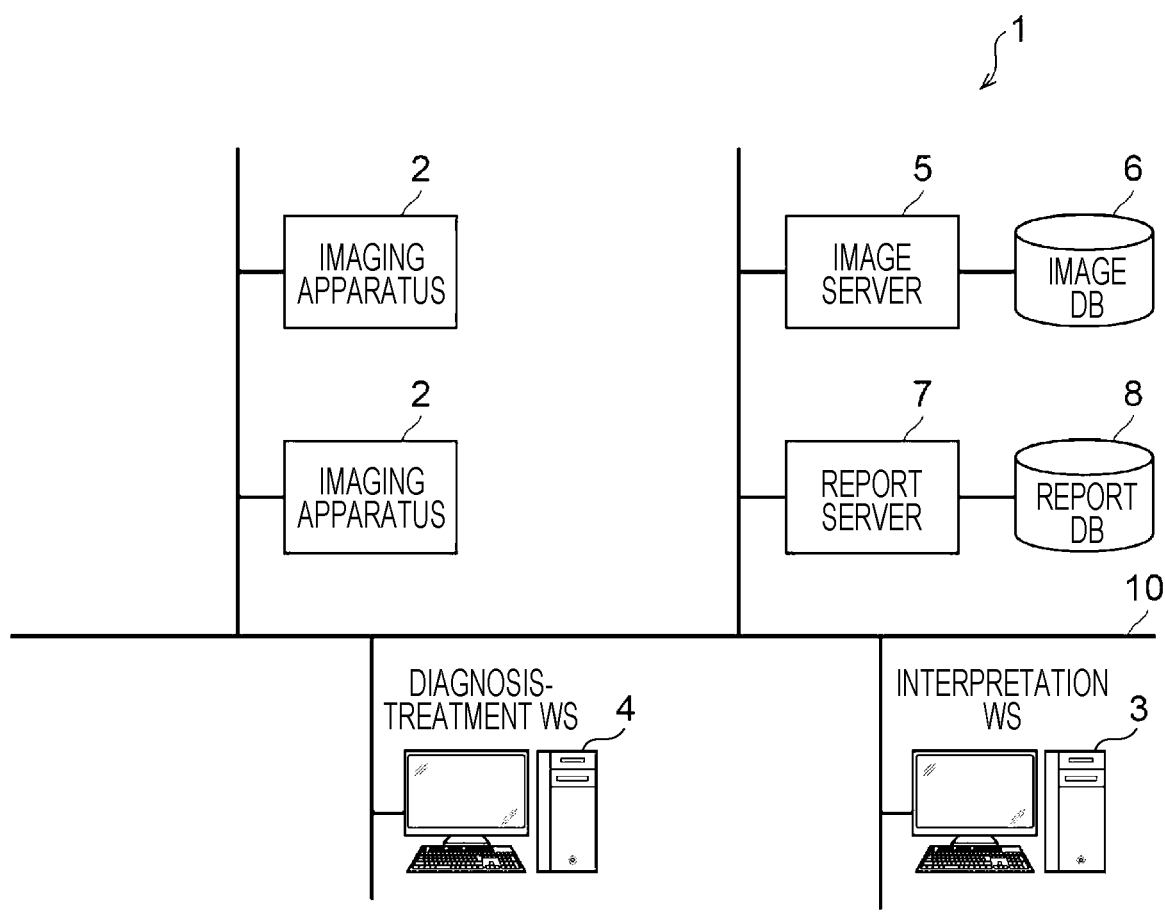
FIG. 1 is a diagram illustrating an example of a schematic configuration of a medical information system to which a document creation apparatus according to a first embodiment is applied.

FIG. 1 is a diagram illustrating a schematic configuration of the medical information system. A medical information system 1 illustrated in FIG. 1 is a system for performing imaging of an examination-target part of a patient who is a photographic subject, based on an examination order given using a publicly known ordering system by a doctor of a diagnosis-treatment department, storing a medical image acquired through the imaging, performing interpretation of the medical image and creation of an interpretation report by a radiologist, and viewing the interpretation report and performing detailed observation of the interpretation-target medical image by the doctor of the diagnosis-treatment department who is a requester.

As illustrated in FIG. 1, in the medical information system 1, a plurality of imaging apparatuses 2, a plurality of interpretation workstations (WSs) 3 that are interpretation terminals, a diagnosis-treatment WS 4, an image server 5, an image database (DB) 6, a report server 7, and a report DB 8 are connected to one another via a wired or wireless network 10 to be able to communicate with one another.

Each device is a computer on which an application program for causing the device to function as a constituent element of the medical information system 1 is installed. The application program is recorded on a recording medium such as a digital versatile disc (DVD) or a compact disc-read only memory (CD-ROM), distributed, and installed on the computer from the recording medium. Alternatively, the application program is stored in a storage device of a server computer connected to the network 10 or a network storage connected to the network to be accessible from the outside, and is downloaded to and installed on the computer in response to a request.

Each of the imaging apparatuses 2 is an apparatus (modality) that images a diagnosis-target part of a patient to generate a medical image representing the diagnosis-target part. Specifically, the imaging apparatuses 2 are a simple X-ray photography apparatus, a CT apparatus, an MRI apparatus, a positron emission tomography (PET) apparatus, and so on. The medical image generated by each of the imaging apparatuses 2 is transmitted to the image server and stored in the image DB 6.

Each of the interpretation WSs 3 is, for example, a computer used by a radiologist of a radiology department to interpret a medical image, create an interpretation report, and so on, and includes a document creation apparatus 20 (details of which will be described later) according to the first embodiment. The interpretation WS 3 issues a request to view a medical image to the image server 5, performs various kinds of image processing on the medical image received from the image server 5, displays the medical image, and accepts input of a finding remark for the medical image. The interpretation WS 3 also performs analysis processing on a medical image, assists creation of an interpretation report based on an analysis result, issues a request to register the interpretation report and a request to view the interpretation report to the report server 7, and displays the interpretation report received from the report server 7. These kinds of processing are performed as a result of the interpretation WS 3 executing a software program for each of the kinds of processing.

The diagnosis-treatment WS 4 is, for example, a computer used by a doctor of a diagnosis-treatment department to perform detailed observation of an image, view an interpretation report, create an electronic medical chart, and so on, and includes a processing device, a display device such as a display, and an input device such as a keyboard and a mouse. The diagnosis-treatment WS 4 issues a request to view an image to the image server 5, displays the image received from the image server 5, issues a request to view an interpretation report to the report server 7, and displays the interpretation report received from the report server 7. These kinds of processing are performed as a result of the diagnosis-treatment WS 4 executing a software program for each of the kinds of processing.

The image server 5 is a general-purpose computer on which a software program for providing functions of a database management system (DBMS) is installed. The image server 5 also includes a storage in which the image DB 6 is configured. This storage may be a hard disk apparatus connected to the image server 5 by a data bus, or may be a disk apparatus connected to a network attached storage (NAS) or a storage area network (SAN) connected to the network 10. In response to receiving a request to register a medical image from the imaging apparatus 2, the image server 5 converts the medical image into a format for the database and registers the resulting medical image in the image DB 6.

In the image DB 6, image data of a medical image acquired by the imaging apparatus 2 and accessory information are registered. The accessory information includes, for example, an image identification (ID) for identifying an individual medical image, a patient ID for identifying a patient, an examination ID for identifying an examination, a unique identification (UID) assigned to each medical image, an examination date and an examination time when the medical image is generated, a type of an imaging apparatus used in the examination to acquire the medical image, patient information such as a name, an age, and a sex of the patient, a part subjected to the examination (imaging), imaging information (such as an imaging protocol, an imaging sequence, an imaging method, an imaging condition, and the use of a contrast medium), and a series number or acquisition number when a plurality of medical images are acquired in a single examination.

In response to receiving a request to view a medical image from the interpretation WS 3 and the diagnosis-treatment WS 4 via the network 10, the image server 5 searches for the medical image registered in the image DB 6 and transmits the retrieved medical image to the interpretation WS 3 and the diagnosis-treatment WS 4 that are requesters.

In the report server 7, a software program for providing functions of a database management system to a general-purpose computer is incorporated. In response to receiving a request to register an interpretation report from the interpretation WS 3, the report server 7 converts the interpretation report into a format for the database and registers the resulting interpretation report in the report DB 8.

In the report DB 8, an interpretation report including a finding remark created by a radiologist using the interpretation WS 3 is registered. The interpretation report may include, for example, information such as an interpretation-target medical image, an image ID for identifying the medical image, a radiologist ID for identifying a radiologist who has performed interpretation, a name of a lesion, position information of the lesion, and properties of the lesion.

In response to receiving a request to view an interpretation report from the interpretation WS 3 and the diagnosis-treatment WS 4 via the network 10, the report server 7 searches for the interpretation report registered in the report DB 8 and transmits the retrieved interpretation report to the interpretation WS 3 and the diagnosis-treatment WS 4 that are requesters.

The network 10 is a wired or wireless local area network that connects various devices in a hospital. When the interpretation WSs 3 are installed in other hospitals or clinics, the network 10 may have a configuration in which local area networks of the individual hospitals are connected to each other via the Internet or a dedicated line.

Figure 2:
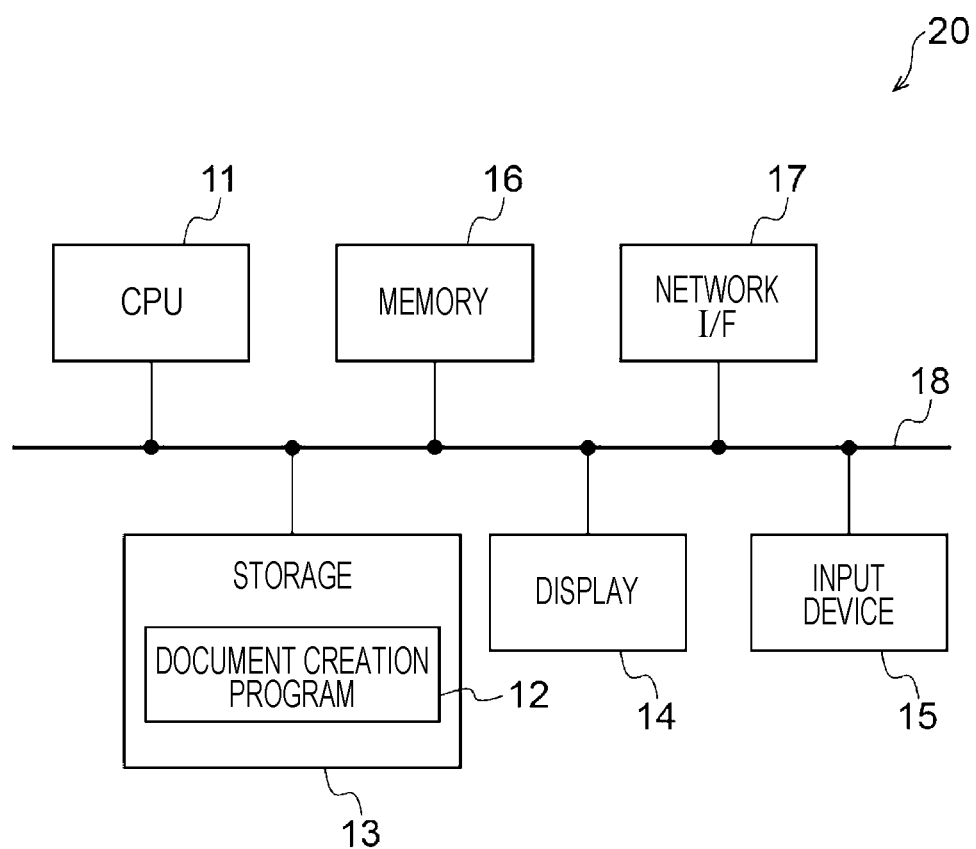
FIG. 2 is a block diagram illustrating an example of a hardware configuration of the document creation apparatus according to the first embodiment.

The document creation apparatus 20 according to the first embodiment will be described next. A hardware configuration of the document creation apparatus 20 according to the first embodiment will be described first with reference to FIG. 2. As illustrated in FIG. 2, the document creation apparatus 20 includes a central processing unit (CPU) 11, a nonvolatile storage 13, and a memory 16 that serves as a temporary storage area. The document creation apparatus 20 also includes a display 14 such as a liquid crystal display, an input device 15 constituted by a keyboard and a pointing device such as a mouse, and a network interface (I/F) 17 connected to the network 10. The CPU 11, the storage 13, the display 14, the input device 15, the memory 16, and network OF 17 are connected to a bus 18. Note that the CPU 11 is an example of a processor in the present disclosure.

The storage 13 is implemented by a hard disk drive (HDD), a solid state drive (SSD), a flash memory, or the like. The storage 13 serving as a storage medium stores a document creation program 12. The CPU 11 reads out the document creation program 12 from the storage 13, loads the document creation program 12 to the memory 16, and executes the loaded document creation program 12.

Figure 3:
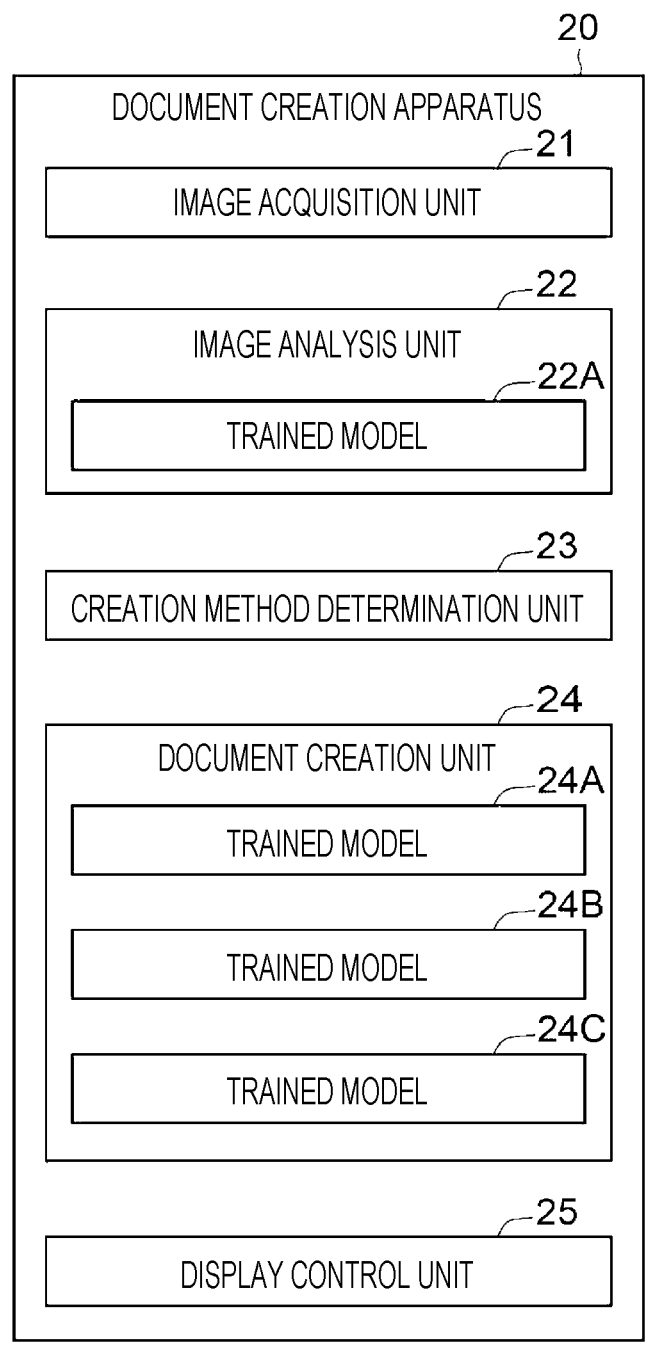
FIG. 3 is a block diagram illustrating an example of a functional configuration of the document creation apparatus according to the first embodiment.

A functional configuration of the document creation apparatus according to the first embodiment will be described next. FIG. 3 is a diagram illustrating a functional configuration of the document creation apparatus according to the first embodiment. As illustrated in FIG. 3, the document creation apparatus 20 includes an image acquisition unit 21, an image analysis unit 22, a creation method determination unit 23, a document creation unit 24, and a display control unit 25. As a result of the CPU 11 executing the document creation program 12, the CPU 11 functions as the image acquisition unit 21, the image analysis unit 22, the creation method determination unit 23, the document creation unit 24, and the display control unit 25.

The image acquisition unit 21 acquires a medical image G0 from the image server 5 via the network OF 17. The medical image G0 is an example of an image. In the first embodiment, as an example, a CT image of the lungs is used as the medical image G0.

The image analysis unit 22 analyzes the medical image G0 to derive an analysis result about a disease or the like included in the medical image G0. Thus, the image analysis unit 22 includes a trained model 22A for which machine learning has been performed to detect an abnormal shadow such as a lesion included in the medical image G0 and obtain a finding about the detected abnormal shadow.

The trained model 22A is prepared, for example, for each organ, identifies an abnormal shadow included in the organ, and obtains a finding about the identified abnormal shadow. Note that findings are obtained for a plurality of finding items. For example, if the organ is the lungs, findings are obtained for a plurality of finding items such as a location of an abnormal shadow included in the lungs, a size of the abnormal shadow, a shape of a boundary (distinct or irregular), a type of an absorption value (solid type or ground glass type), the presence or absence of a spicula, whether the abnormal shadow is a mass or a nodule, the presence or absence of pleural contact, the presence or absence of pleural indentation, the presence or absence of pleural infiltration, the presence or absence of a cavity, and the presence or absence of calcification. Note that the finding items are an example of attribute information about findings in the present disclosure.

In the present embodiment, the trained model 22A is constituted by a convolutional neural network (CNN) for which deep learning has been performed to obtain a finding for an abnormal shadow included in the medical image G0.

The trained model 22A is built through machine learning by using, as training data, combinations of a medical image including an abnormal shadow and findings for various finding items related to the abnormal shadow, for example. In response to receiving a medical image, the trained model 22A outputs a score (hereinafter, referred to as a finding score) for a finding derived for each finding item in an abnormal shadow included in the medical image. The finding score is a score indicating a saliency of a finding for each finding item. The finding score takes a value from 0 to 1, for example. The greater the value of the finding score is, the more salient the finding for the finding item is.

For example, if the finding score for "the presence or absence of a spicula" which is one of the finding items of the abnormal shadow is, for example, 0.5 or greater, the finding for "the presence or absence of a spicula" of the abnormal shadow indicates that "the presence of a spicula (positive)". If the finding score for "the presence or absence of a spicula" is, for example, less than 0.5, the finding for "the presence or absence of a spicula" of the abnormal shadow indicates "the absence of a spicula (negative)". Note that a threshold value of 0.5 used to obtain a finding is merely an example, and is set to an appropriate value for each finding item.

FIG. 4 is a diagram illustrating an example of findings included in an analysis result derived by the image analysis unit 22. FIG. 4 illustrates an example of findings when the medical image G0 is a CT image of the lungs. When the medical image G0 is a CT image of the lungs, the image analysis unit 22 derives findings "under the pleura of the left lung", "4.2 cm", "irregular", "solid type", "spicula: positive", "mass", "pleural contact: positive", "pleural indentation: positive", "pleural infiltration: negative", "cavity: negative", and "calcification: negative" for a plurality of finding items, for example. In FIG. 4, "+" is given in the case of "present", that is, positive, and "−" is given in the case of "absent", that is, negative.

Note that as the trained model 22A, any trained model such as a support vector machine (SVM), for example, can be used in addition to a convolutional neural network.

Based on criterion information for determining output of a document, the creation method determination unit 23 determines output of a document to be created. In the first embodiment, the creation method determination unit 23 determines a creation method of a document about the medical image G0 to determine output of the document. In the first embodiment, the creation method determination unit 23 determines the creation method of a medical document, based on the number of finding items included in the analysis result derived by the image analysis unit 22. The number of finding items is an example of criterion information, more specifically, an evaluation criterion for determining a creation method in the present disclosure. In the first embodiment, the document is a finding remark about the medical image G0.

In the first embodiment, for each part included in the medical image G0, a table in which the number of finding items is associated with a document creation method is prepared and stored in the storage 13. FIG. 5 is a diagram illustrating an example of the table in which the number of finding items is associated with the document creation method. In a table 30 illustrated in FIG. 5, cases where the number of finding items is one, two, and three are associated with templates T1, T2, and T3, respectively. A case where the number of finding items is four is associated with natural language processing NLP1. A case where the number of finding items is five is associated with natural language processing NLP2. A case where the number of finding items is six or more is associated with three kinds of natural language processing NLP1 to NLP3.

The templates T1 to T3 each are constituted by a text having blank fields according to the number of finding items. For example, the template T2 is a text having blank fields to which two findings can be inserted, such as "The <finding> is visible in the <location>.". The kinds of the natural language processing NLP1 to NLP3 each correspond to a creation method of a document using a trained model built as a result of training of a neural network.

The creation method determination unit 23 determines a creation method of a document, based on the number of finding items included in the analysis result with reference to the table 30. For example, if the number of finding items is two, the creation method determination unit 23 determines the template T2 as the creation method. If the number of finding items is six or more, the creation method determination unit 23 determines the three kinds of natural language processing NLP1 to NLP3 as the creation method.

Note that the table referred to by the creation method determination unit 23 is not limited to the one illustrated in FIG. 5. For example, a table in which whether to use a template or natural language processing is associated with a part identified by finding items may be used. In this case, for example, if the part is the lungs, the number of finding items included in the analysis result is large. Thus, natural language processing may be associated as the creation method. If the part is the pancreas, the number of finding items included in the analysis result is small. Thus, a template may be associated as the creation method.

When the part is identified, an examination instruction document used at the time of acquisition of the medical image G0 may be referred to instead of the finding items. Since the name of the part subjected to the examination is written in the examination instruction document, the part may be identified by the name of the part written in the examination instruction document. Examination items are also written in the examination instruction document. The examination items differ from disease to disease. Therefore, the disease may be identified or the part may be identified from the disease, with reference to the examination items written in the examination instruction document. Note that the examination instruction document is stored in the image server 5 in association with the medical image G0, for example, and may be acquired together with the medical image G0 when the image acquisition unit 21 acquires the medical image G0 from the image server 5.

The creation method determination unit 23 may determine the creation method in accordance with the number of abnormal shadows included in the analysis result. For example, the creation method determination unit 23 may determine the template as the creation method when the analysis result includes only findings for a single abnormal shadow, and determine the natural language processing as the creation method when the analysis result includes findings for a plurality of abnormal shadows.

Alternatively, an evaluation value determined in advance for each part and disease may be stored in the storage 13, and the creation method may be determined in accordance with the evaluation value. FIG. 6 is a diagram illustrating a table indicating a relationship between a part and disease and an evaluation value. FIG. 7 is a diagram illustrating a table in which an evaluation value is associated with a creation method of a document. As illustrated in FIG. 6, in a table 31, the evaluation value is associated with the part and disease. As the evaluation value, for example, an evaluation value representing a difficulty of creating a document can be used. Specifically, the evaluation value is defined by a value from 0 to 1, and the table 31 can be created such that the higher the difficulty of creating a document is, the greater the evaluation value is. Note that the difficulty of creating a document is an example of a predetermined evaluation criterion for determining a creation method in the present disclosure, and the evaluation value indicating the difficulty is an example of an evaluation result according to the criterion information in the present disclosure.

Since the disease of the lungs or the liver is likely to be complicated, there are many finding items to be written in a finding remark. Additionally, there are many finding items to be written in a finding remark for a highly malignant disease. Further, findings for different diseases may be collectively written in a single sentence. In such cases, the difficulty of creating a document increases. Thus, the evaluation value may be set to a large value for a part where the disease is likely to be complicated, for a highly malignant disease, or the like. For example, in the table 31 illustrated in FIG. 6, the evaluation value may be defined to be 1.0 if the part is the lungs and the liver, and the evaluation value may be defined to be 0.5 if the part is other than the lungs and the liver. Additionally, the evaluation value may be defined to be 1.0 when the disease is cancer, and the evaluation value may be defined to be 0.5 when the disease is other than cancer.

On the other hand, as illustrated in FIG. 7, the evaluation value is associated with the creation method in a table 32. In FIG. 7, the natural language processing NLP1 is associated with the evaluation value X1. The templates T1 and T2 are respectively associated with the evaluation values X2 and X3. The template T1 and the natural language processing NLP1 (T1+NLP1) are associated with the evaluation value X4.

The creation method determination unit 23 acquires the evaluation value corresponding to the part and disease, based on the analysis result with reference to the table 31. The creation method determination unit 23 then determines the creation method of a document, in accordance with the acquired evaluation value with reference to the table 32. In this case, the creation method of a document may be determined by using an evaluation value obtained by adding up the evaluation values for the part and the disease. For example, in the case of the lung cancer, the creation method of a document may be determined using an evaluation value of 2.0 which is a sum of an evaluation value for the lungs and an evaluation value for the cancer.

Findings for all the finding items included in the analysis result may not be written in a finding remark. For example, some of the findings may be written in an already created finding remark. In such a case, the number of findings to be written in a finding remark to be created reduces. In such a case, the difficulty represented by the evaluation value acquired with reference to the table 31 may be reduced, and the creation method of a document may be determined.

Additionally, an instruction to collectively write a plurality of findings in a single finding remark may be given. In such a case, the difficulty represented by the evaluation value acquired with reference to the table 31 may be increased, and the creation method of a document may be determined.

Alternatively, the creation method may be determined in accordance with a predetermined condition. For example, in accordance with a predetermined condition, one creation method is determined from among the creation method based on the number of finding items included in the analysis result, the creation method based on the number of abnormal shadows included in the analysis result, and the creation method based on the evaluation value predetermined for each part and disease. Examples of the predetermined condition include an organ included in the medical image G0 being a specific organ such as the lungs or the liver, the medical image G0 including a specific finding, the medical image G0 being captured with a specific imaging apparatus, and patient information such as the sex and age of the patient for whom the medical image G0 is acquired satisfying a specific condition.

The document creation unit 24 creates at least one finding remark including the analysis result by using the creation method determined by the creation method determination unit 23. The finding remark is an example of a document in the present disclosure. The at least one finding remark created by the document creation unit 24 is an example of at least one document in the present disclosure. Suppose that the findings included in the analysis result are three, i.e., "right lung S1", "1 cm", and "mass", and the template T3 having three blank fields is determined as the creation method. The template T3 is, for example, a text "A <type> of <size> in size is visible in the <location>.". In this case, the document creation unit 24 creates a finding remark "A <mass> of <1 cm> in size is visible in the <right lung S1>.".

The document creation unit 24 includes trained models 24A to 24C each of which has been trained to generate a finding remark by using at least one finding included in the analysis result. The trained models 24A to 24C respectively correspond to the kinds of natural language processing NLP1 to NLP3.

As the trained models 24A to 24C, for example, recurrent neural networks can be used. To output a finding remark from the analysis result obtained by the image analysis unit 22, each of the trained models 24A to 24C is built by performing machine learning of a recurrent neural network by using many pieces of training data constituted by combinations of finding items included in the analysis result and a finding remark. If the creation method of a document determined by the creation method determination unit 23 is the natural language processing, the document creation unit 24 inputs at least one finding included in the analysis result to the trained models 24A to 24C to cause the trained models 24A to 24C to output finding remarks.

For example, when the analysis result obtained by the image analysis unit 22 includes four findings "left lung S6", "1.5 cm", "nodule", and "pulmonary metastasis", the creation method determination unit 23 determines the natural language processing NLP2 as the creation method. By using the trained model 24B corresponding to the natural language processing NPL2, the document creation unit 24 creates a finding remark "A nodule of 1.5 cm in size is visible in the left lung S6, and the pulmonary metastasis is suspected.".

When the creation method determination unit 23 determines a plurality of kinds of natural language processing as the creation method, the document creation unit 24 creates a plurality of finding remarks using the plurality of kinds of natural language processing.

For example, suppose that the analysis result of the medical image G0 includes findings for six finding items "upper lobe of the left lung", "pleural indentation: positive", "irregular margin: positive", "spicula: positive", "4.2 cm", and "mass". In this case, the creation method determination unit 23 determines the three kinds of natural language processing NLP1 to NLP3 as the creation method. The trained models 24A to 24C respectively corresponding to the kinds of natural language processing NPL1 to NPL3 generate different finding remarks in each of which at least one of the plurality of findings is written. The trained models 24A to 24C generate a plurality of finding remarks such that at least one of the findings for the plurality of finding items is written in the respective finding remarks and combinations of the finding items corresponding to the findings written in the plurality of finding remarks are different from one another among the plurality of finding remarks. In this case, the plurality of finding remarks are an example of documents different in both the findings and the creation method used for creation. The plurality of finding remarks may be different only in the findings used for creation, or may be different only in the creation method.

For example, the trained model 24A corresponding to the natural language processing NLP1 may generate a finding remark "A mass is visible in the upper lobe of the left lung.", based on for example "the upper lobe of the left lung" and "mass" among the findings identified for the plurality of finding items. In addition, the trained model 24B corresponding to the natural language processing NLP2 generates a finding remark "A mass of 4.2 cm in size with pleural indentation is visible in the upper lobe of the left lung.", based on for example "upper lobe of the left lung", "pleural indentation: positive", "4.2 cm", and "mass" among the findings identified for the plurality of finding items. In addition, the trained model 24C corresponding to the natural language processing NLP3 generates a finding remark "A spiculated mass with pleural indentation is visible in the upper lobe of the left lung.", based on for example "upper lobe of the left lung", "pleural indentation: positive", "spicula: positive", and "mass" among the findings identified for the plurality of finding items.

When the creation method determination unit 23 determines T1+NLP1 illustrated in FIG. 7 as the creation method, the document creation unit 24 creates a finding remark by using the template T1 and the natural language processing NLP1 in combination. In this case, the document creation unit 24 creates a relatively simple finding remark based on the template by using some of the plurality of findings included in the analysis result. For the rest of the findings, the document creation unit 24 creates a finding remark by using the natural language processing. For example, suppose that the analysis result includes "5 mm", "nodule", "spiculated margin: positive", "internal calcification: positive", "pleural contact: positive", and "pleural infiltration: positive". In this case, by using the template T1 for the findings "5 mm" and "nodule", the document creation unit 24 creates a finding remark "A nodule of 5 mm is visible in the lung.". Then, by using the trained model 24A corresponding to the natural language processing NLP1 for the findings of "spiculated margin: positive", "internal calcification: positive", "pleural contact: positive", and "pleural infiltration: positive", the document creation unit 24 creates a finding remark "A spiculated margin and internal calcification are visible. Additionally, the pleural contact is present, and the pleural infiltration is suspected.".

When the creation method determination unit 23 determines T1+NLP1 illustrated in FIG. 7 as the creation method, the document creation unit 24 may create a finding remark by using the natural language processing NLP1 for main findings and create a finding remark by using the template T1 for additional information. For example, suppose that the analysis result includes "5 mm", "nodule", "spiculated margin: positive", "internal calcification: positive", "pleural contact: positive", "pleural infiltration: positive", and "compression of pulmonary vessels: positive". In this case, "5 mm", "nodule", "spiculated margin: positive", "internal calcification: positive", "pleural contact: positive", and "pleural infiltration: positive" are the main findings. "Compression of pulmonary vessels: positive" is the additional finding. By using the trained model 24A corresponding to the natural language processing NLP1 for the main findings, the document creation unit 24 creates a finding remark "A nodule of 5 mm is visible in the lung. A spiculated margin and internal calcification are visible. Additionally, the pleural contact is present, and the pleural infiltration is suspected.". By using the template T1 for "compression of pulmonary vessels: positive" which is the additional finding, the document creation unit 24 creates a finding remark "Compression of pulmonary vessels is visible.".

Figure 8:
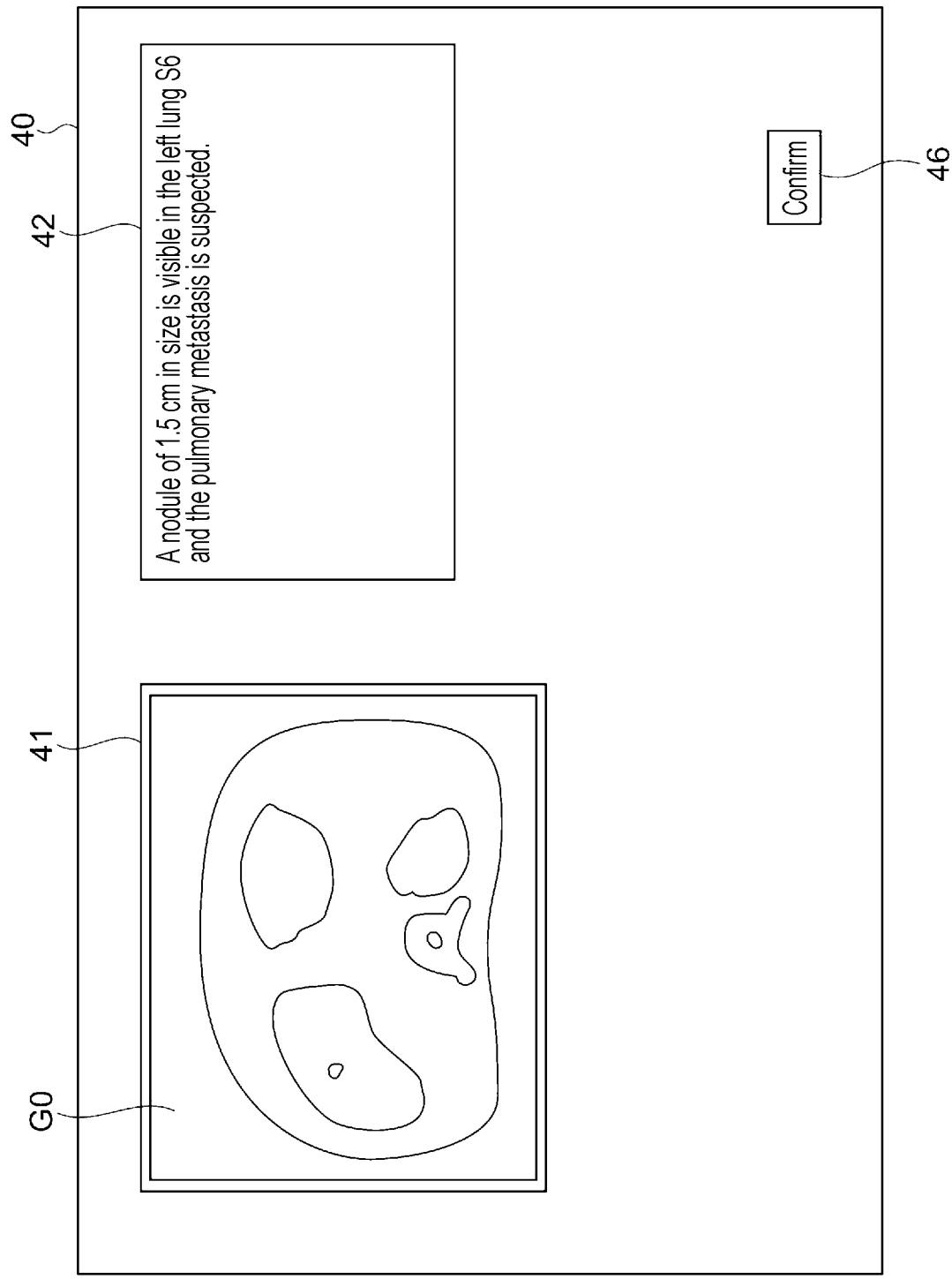
FIG. 8 is a diagram illustrating a finding remark display screen in the first embodiment.

The display control unit 25 displays the created finding remark on the display 14. FIG. 8 is a diagram illustrating a finding remark display screen. As illustrated in FIG. 8, a display screen 40 includes an image display area 41 and a document display area 42. The medical image G0 is displayed in the image display area 41. When the medical image G0 is a three-dimensional image such as a CT image, a tomographic image of one tomographic plane included in the three-dimensional image is displayed in the image display area 41. The finding remark created by the document creation unit 24 is displayed in the document display area 42. Note that the finding remark is "A nodule of 1.5 cm in size is visible in the left lung S6 and the pulmonary metastasis is suspected.".

Figure 9:
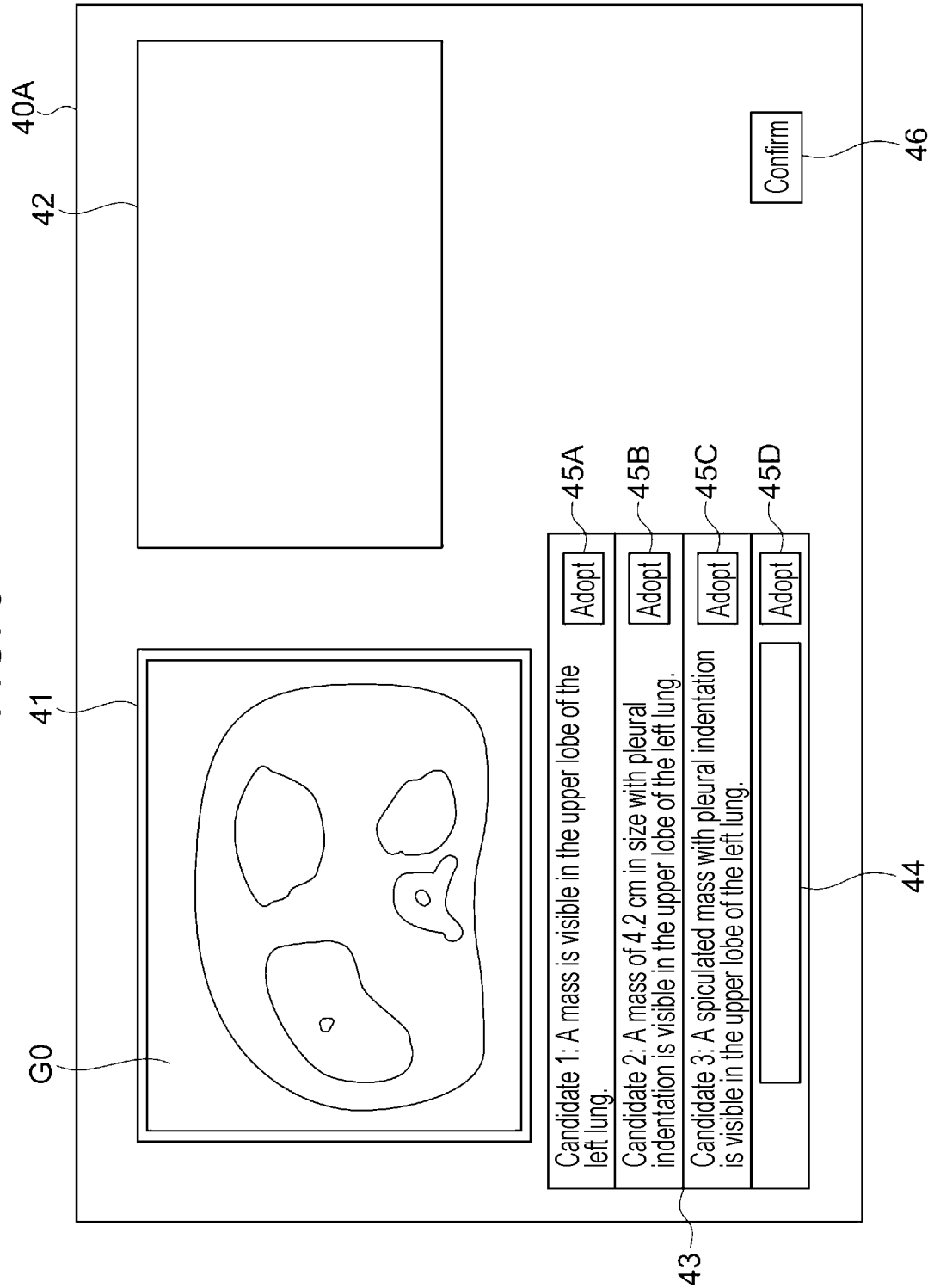
FIG. 9 is a diagram illustrating the finding remark display screen in the first embodiment.

FIG. 9 illustrates a finding remark display screen when the creation method determination unit 23 determines a plurality of creation methods. When a plurality of creation methods are determined, a plurality of finding remarks are created accordingly. Thus, a display screen 40A illustrated in FIG. 9 displays a finding remark display area 43 for displaying the plurality of finding remarks. A plurality of (three in this case) candidate finding remarks are displayed in the finding remark display area 43. In addition to the three finding remarks, a free input field 44 is also displayed. Adopt buttons 45A to 45D are respectively displayed on the right side of the candidate finding remarks and the free input field 44.

The radiologist can correct the finding remark by using the input device 15 if necessary. When a plurality of finding remarks are displayed, the radiologist selects an adopt button corresponding to the desired finding remark. Consequently, the selected finding remark is displayed in the document display area 42. On the other hand, if a finding remark matching an interpretation result of a lesion included in the medical image G0 is not displayed in the finding remark display area 43, the radiologist inputs the finding remark in the free input field 44 by themselves, and selects the adopt button 45D. Consequently, the finding remark input to the free input field 44 by the radiologist is displayed in the document display area 42.

When the radiologist selects a confirm button 46, an interpretation report including the finding remark displayed in the document display area 42 is created. The created interpretation report is stored in the storage 13 together with the medical image G0 and the analysis result. Thereafter, the created interpretation report is transferred to the report server 7 together with the medical image G0 and the analysis result. The report server 7 stores the transferred interpretation report together with the medical image G0 and the analysis result.

Figure 10:
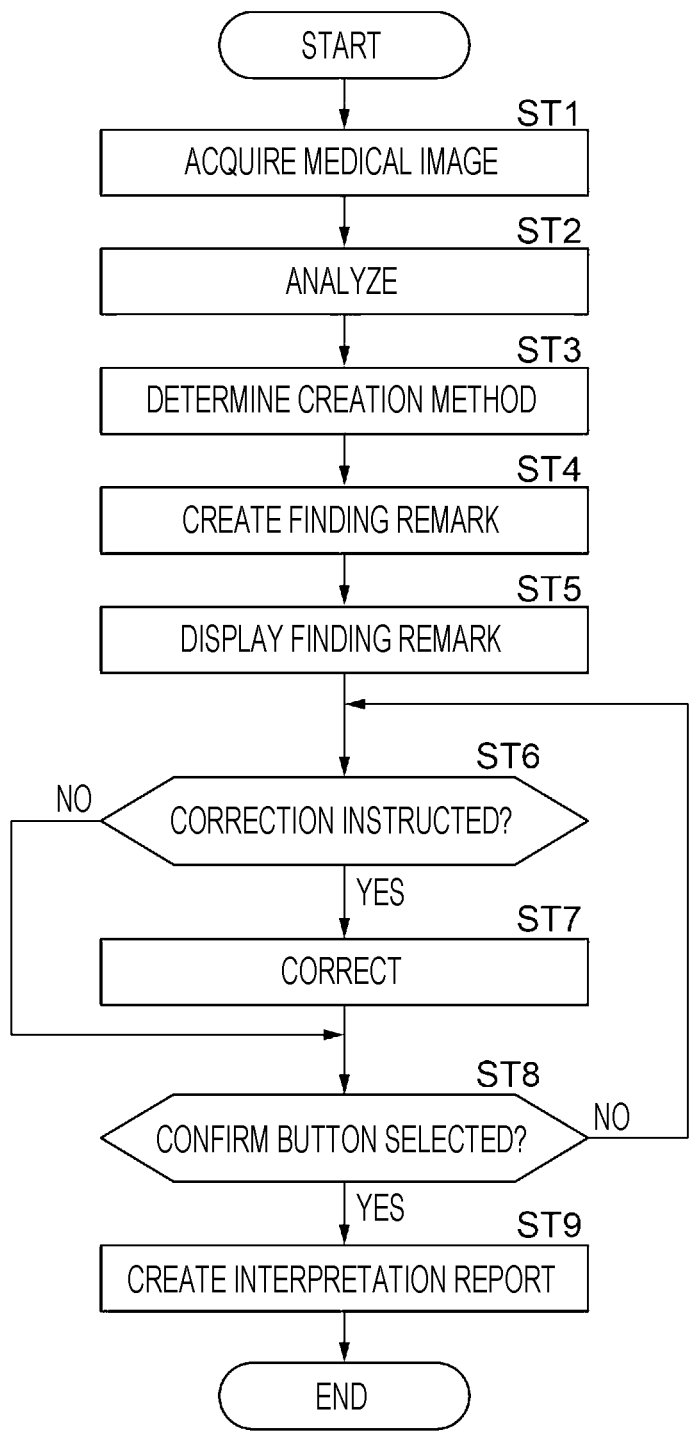
FIG. 10 is a flowchart illustrating a process performed in the first embodiment.

A process performed in the first embodiment will be described next. FIG. 10 is a flowchart illustrating the process performed in the first embodiment. In response to an instruction to start the process from the input device 15, the image acquisition unit 21 acquires the medical image G0 from the image server 5 (step ST1). Subsequently, the image analysis unit 22 analyzes the medical image G0 to acquire an analysis result including at least one finding (step ST2). Subsequently, based on the analysis result, the creation method determination unit 23 determines at least one creation method of a document about the medical image G0 (step ST3).

The document creation unit 24 then creates at least one finding remark by using the determined creation method (step ST4). The display control unit 25 displays the finding remark on the display 14 (step ST5). Subsequently, the document creation unit 24 determines whether or not an instruction to correct the finding remark is issued (step ST6). If YES in step ST6, the document creation unit 24 corrects the finding remark (step ST7). The process then proceeds to the processing of step ST8.

If NO in step ST6, the document creation unit 24 determines whether or not the confirm button 46 is selected (step ST8). If NO in step ST8, the process returns to step ST6 and the processing of step ST6 and thereafter is repeated. If YES in step ST8, an interpretation report is created (step ST9). The process then ends. The created interpretation report is stored in the storage 13 together with the medical image G0 and the analysis result. The created interpretation report is also transferred to the report server 7 together with the medical image G0 and the analysis result.

As described above, in the present embodiment, the creation method of a finding remark about the medical image G0 is determined based on criterion information, i.e., the analysis result of the medical image G0, for determining output of a document, and a finding remark is created by using the determined creation method. Thus, the creation method of a finding remark can be adaptively determined in accordance with the criterion information. For example, in accordance with the number of finding items included in the analysis result that is the criterion information, the creation method of a finding remark can be determined as a template or natural language processing. Thus, templates for a large number of finding items no longer need to be prepared as the creation methods of a finding remark. In addition, natural language processing for a small number of finding items no longer needs to be prepared. Therefore, in the present embodiment, the finding remark about the medical image G0 can be created with a simple configuration.

Figure 11:
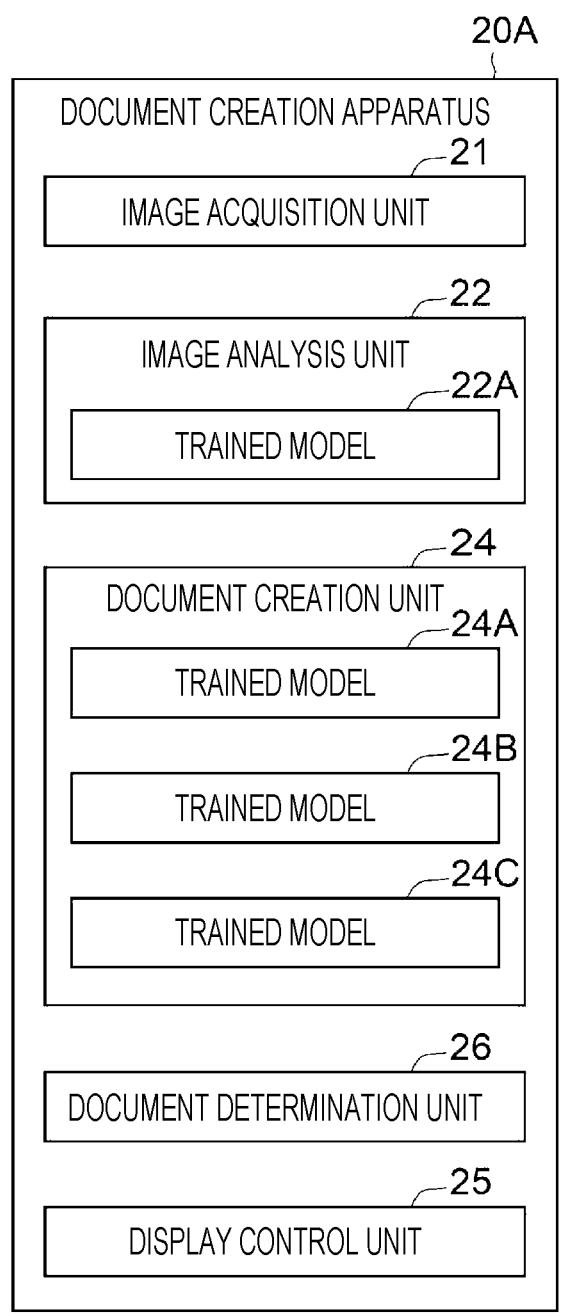
FIG. 11 is a block diagram illustrating an example of a functional configuration of a document creation apparatus according to a second embodiment.

A second embodiment of the present disclosure will be described next. FIG. 11 is a diagram illustrating a functional configuration of a document creation apparatus according to the second embodiment. In FIG. 11, the same components as those in FIG. 3 are denoted by the same reference signs, and a detailed description thereof is omitted. A document creation apparatus 20A according to the second embodiment is different from the first embodiment in that the document creation apparatus 20A includes a document determination unit 26 instead of the creation method determination unit 23 of the document creation apparatus 20 according to the first embodiment.

In the second embodiment, the document creation unit 24 creates a plurality of (three in this case) finding remarks including at least one finding included in an analysis result, by using the trained models 24A to 24C corresponding to kinds of natural language processing NLP1 to NLP3, respectively. As in the first embodiment, the trained models 24A to 24C have been trained to create finding remarks by using the kinds of natural language processing NLP1 to NLP3 different from one another, respectively. In the second embodiment, based on criterion information, the document determination unit 26 determines at least one finding remark of the plurality of finding remarks as a document to be output. In the second embodiment, reliability indicating document appropriateness is used as the criterion information. The reliability will be described below.

Figure 12:
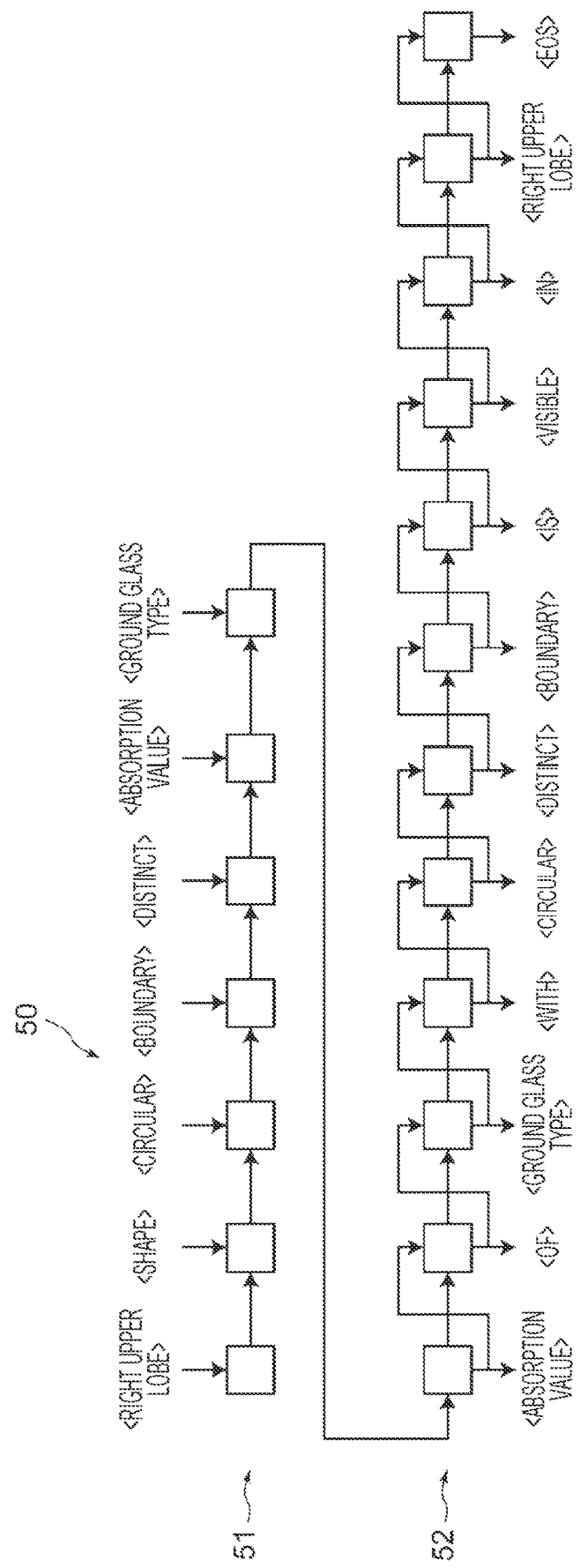
FIG. 12 is a diagram schematically illustrating a recurrent neural network.

FIG. 12 is a diagram schematically illustrating a recurrent neural network used as the trained models 24A to 24C included in the document creation unit 24. As illustrated in FIG. 12, a recurrent neural network 50 includes an encoder 51 and a decoder 52. The encoder 51 includes a plurality of input layers, and at least one of the findings included in the analysis result is input to each of the input layers. In FIG. 12, findings "right upper lobe", "shape", "circular", "boundary", "distinct", "absorption value", and "ground glass type" are input to the encoder 51. The decoder 52 has been trained to convert text information into a sentence, and creates a finding remark from the text information of the input findings. Specifically, from the above-described text information representing the findings "right upper lobe", "shape", "circular", "boundary", "distinct", "absorption value", and "ground glass type", the decoder 52 creates a finding remark "Absorption value of ground glass type with circular distinct boundary is visible in right upper lobe.".

When creating the finding remark, words to be included in the finding remark are output from the respective layers of the decoder 52 in an order in which the words are to be included in the finding remark. At this time, in each layer, scores for a plurality of words that can be output from the layer are derived, and a word having the highest score is output from the layer. For example, a layer subsequent to layers that have output "absorption value" and "of" can output words representing the plurality of findings "circular", "boundary", "distinct", "absorption value" and "ground glass type". FIG. 12 illustrates a state in which "ground glass type" is output since "ground glass type" has the highest score as a result of deriving scores for those findings.

In the second embodiment, for each of a plurality of finding remarks created by the document creation unit 24, the document determination unit 26 derives a representative value of the scores for the words representing the findings output by the plurality of layers of the decoder 52, as the reliability indicating the document appropriateness. As the representative value, an average value, a maximum value, a minimum value, an intermediate value, or the like of the scores derived for the words output from the respective layers can be used. Then, the document determination unit 26 determines at least one finding remark for which the reliability satisfies a criterion among the plurality of created finding remarks, as the document to be output. As the criterion, the reliability showing the largest value, the reliability being greater than or equal to a predetermined threshold value, the reliability being at top n ranks, or the like can be used.

For example, suppose that by using the trained models 24A to 24C, the document creation unit 24 creates three finding remarks "A mass is visible in the upper lobe of the left lung.", "A mass of 4.2 cm in size with pleural indentation is visible in the upper lobe of the left lung.", and "A spiculated mass with pleural indentation is visible in the upper lobe of the left lung." which are the same as the candidates 1 to 3 illustrated in FIG. 9, respectively. Suppose that scores of the three candidates 1, 2, 3 for the finding remark are 0.8, 0.7, and 0.6, respectively. Suppose that a threshold value serving as the criterion of the reliability is greater than or equal to 0.7. The document determination unit 26 determines, as the document to be output, the candidates 1 and 2 whose score is greater than or equal to the threshold value of 0.7 among the candidates 1 to 3.

Note that the document determination unit 26 may be provided with a trained model that has been trained to determine fluency of a plurality of finding remarks created by the document creation unit 24, and may determine a document to be output, by using the fluency as the reliability indicating the document appropriateness. In this case, the document creation unit 24 may create finding remarks by using not only natural language processing but also templates.

Figure 13:
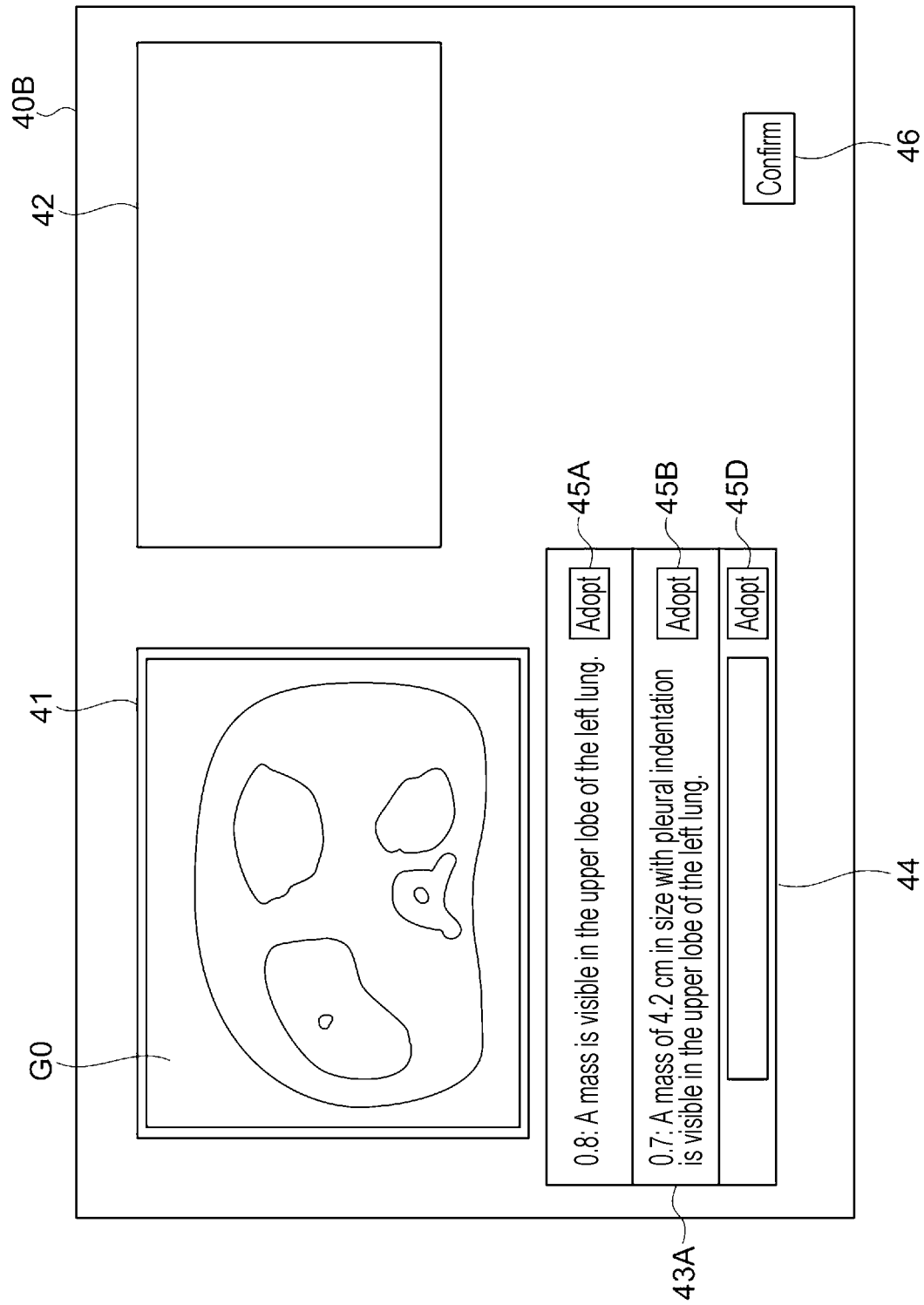
FIG. 13 is a diagram illustrating a finding remark display screen in the second embodiment.

FIG. 13 is a diagram illustrating a finding remark display screen in the second embodiment. As illustrated in FIG. 13, in a display screen 40B in the second embodiment, at least one (two in FIG. 13) finding remark determined by the document determination unit 26 as a document to be output is displayed in a finding remark display area 43A. The two finding remarks are assigned respective evaluation values of 0.8 and 0.7.

In the display screen 40B, the radiologist can select a desired finding remark from the plurality of finding remarks displayed in the finding remark display area 43A, with reference to the evaluation values assigned to the respective displayed finding remarks. Note that the input to the free input field 44 and the processing performed in response to selection of the confirm button 46 are the same as those in the first embodiment, and thus a detailed description thereof is omitted here.

Figure 14:
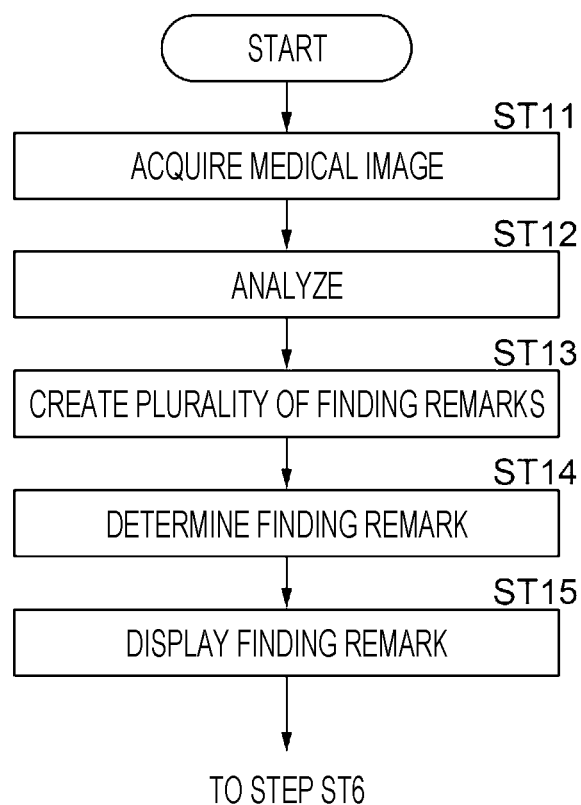
FIG. 14 is a flowchart illustrating a process performed in the second embodiment.

A process performed in the second embodiment will be described next. FIG. 14 is a flowchart illustrating the process performed in the second embodiment. In response to an instruction to start the process from the input device 15, the image acquisition unit 21 acquires the medical image G0 from the image server 5 (step ST11). Subsequently, the image analysis unit 22 analyzes the medical image G0 to acquire an analysis result including at least one finding (step ST12). Subsequently, the document creation unit 24 creates a plurality of finding remarks (step ST13). Then, the document determination unit 26 determines, as a document to be output, at least one finding remark among the plurality of finding remarks, based on the criterion information (step ST14). The process then proceeds to step ST6 illustrated in FIG. 10. Note that the processing of step ST6 and thereafter is the same as that in the first embodiment, and a detailed description thereof is omitted here.

Note that in the first embodiment, the number of finding items included in the analysis result is used as the criterion information for determining the creation method of a document. However, the criterion information is not limited to this. For example, the creation method of a document may be determined based on the number of positive findings or the number of negative findings among the findings included in the analysis result in addition to or instead of the number of finding items.

In the first embodiment, the number of finding items is used as the criterion information. However, the criterion information is not limited to this. For example, an image of an abnormal shadow region detected in the medical image G0 may be used as the criterion information. In this case, for example, a database (hereinafter, referred to as a management DB) is prepared in which abnormal shadow regions extracted from various medical images are associated with a plurality of findings or finding items, and the creation method of a finding remark is determined with reference to this database.

FIG. 15 is a diagram illustrating an example of the management DB. As illustrated in FIG. 15, a plurality of pieces of correspondence information each associating a plurality of findings, finding items, and a creation method of a document one another are registered in the management DB 55. Each of the pieces of correspondence information includes a part, a disease type, a disease name, a plurality of disease features, anatomical level information, size level information, and medical image information. In each of the pieces of correspondence information, the disease features, the anatomical level information, the size level information, the medical image information, and the creation method are associated with each part, disease type, or disease name.

The disease features are findings acquired through analysis of the medical image when the management DB 55 is created. FIG. 15 illustrates three disease features for a single disease type or disease name. However, the number of disease features depends on the number of acquired findings. The anatomical level information is information representing a level of an anatomical segment of an organ in which the abnormal shadow exists. The size level information is information indicating the measurement direction of the size of the abnormal shadow and the magnitude of the size.

The medical image information represents a local image of the abnormal shadow region included in the medical image from which the finding(s) registered in each of the pieces of correspondence information has (have) been acquired. In FIG. 15, a quadrangle each representing a local image indicates that a local image of the medical image is registered. Note that a single piece of correspondence information may include a plurality of pieces of medical image information as illustrated in FIG. 15.

When the management DB 55 is used, the image analysis unit 22 extracts a local image of an abnormal shadow region from the medical image G0 as the criterion information. Then, the creation method determination unit 23 derives a similarity between the local image of the abnormal shadow and the medical image information included in each of the pieces of correspondence information with reference to the management DB 55. Then, the creation method determination unit 23 determines the creation method of a document registered in at least one piece of correspondence information whose similarity satisfies a criterion, as the creation method of the finding remark about the target medical image G0. As the criterion, the similarity showing the largest value, the similarity being greater than or equal to a predetermined threshold value, the similarity being at top m ranks, or the like can be used.

Then, the document creation unit 24 creates at least one finding remark by using the creation method determined by the creation method determination unit 23. In this case, a finding or finding item registered in the at least one piece of correspondence information whose similarity satisfies the criterion may be used as the finding to be included in the finding remark.

Figure 16:
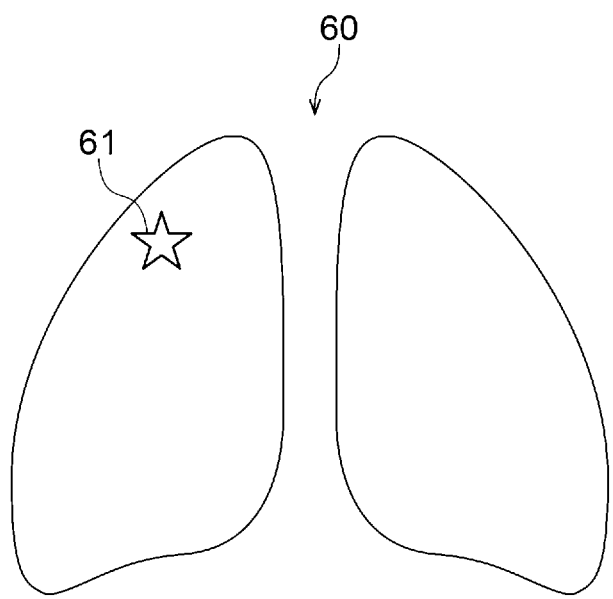
FIG. 16 is a diagram illustrating an example of a document including a graphical representation of an analysis result.

In each of the embodiments described above, the document creation unit 24 creates a finding remark including an analysis result. However, the document created is not limited to this. A document including a graphical representation of the analysis result may be created. FIG. 16 is a diagram illustrating an example of the document including the graphical representation of the analysis result. Suppose that the analysis result includes findings "upper lobe of the right lung" and "pulmonary nodule". In this case, the document creation unit 24 may select a schema 60 of the lungs as the creation method based on the analysis result, and generate, as graphical information, a document in which a marking 61 is added at a position in the upper lobe of the right lung in the schema 60 of the lungs. Generating and displaying a document including such a graphical representation enables the position of the abnormal part to be recognized easily.

Figure 17:
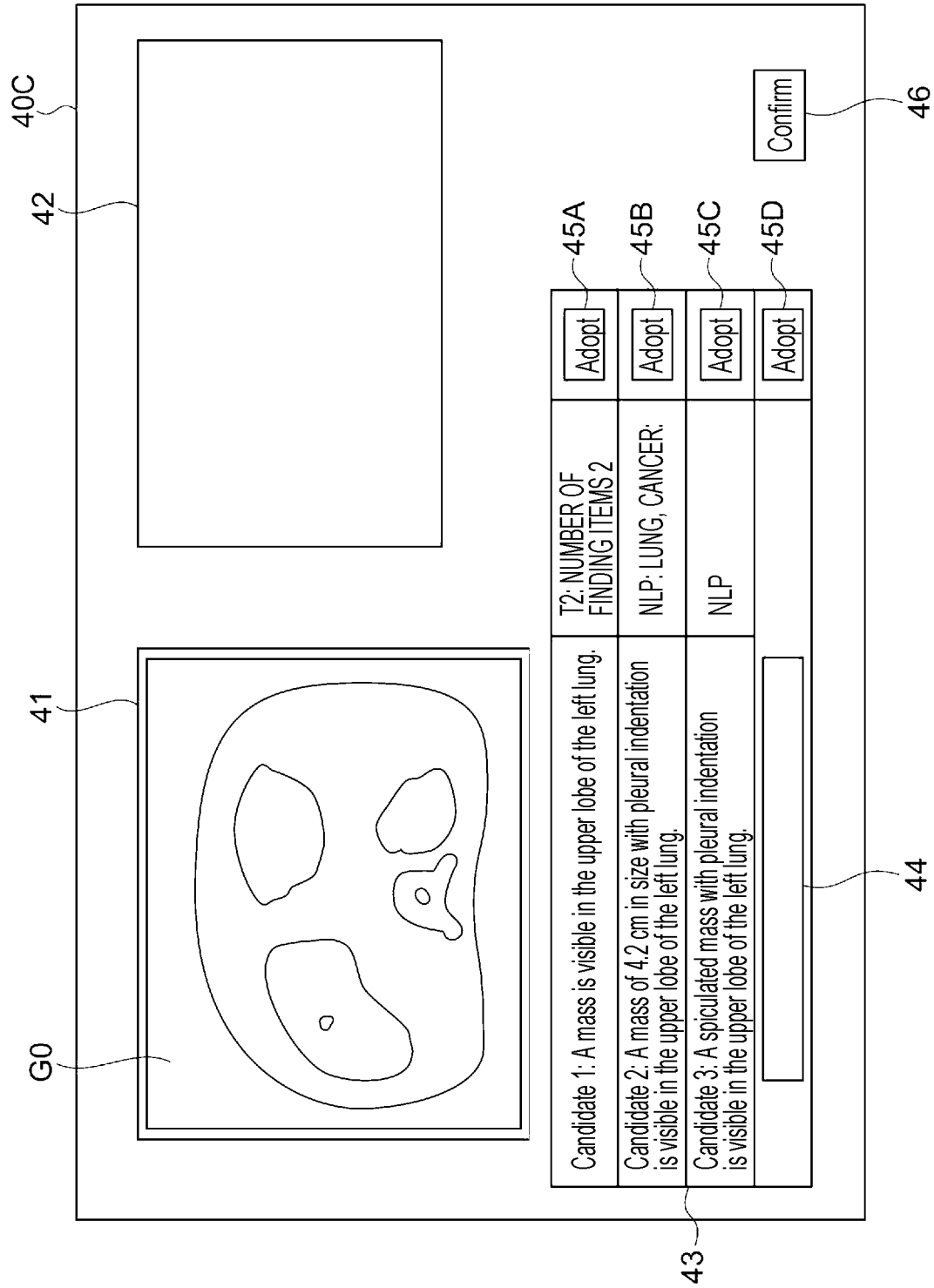
FIG. 17 is a diagram illustrating another example of the finding remark display screen.

In each of the embodiments described above, at least one of the creation method of a finding remark or the criterion information may be displayed in association with the finding remark displayed in the finding remark display screen. For example, as illustrated in FIG. 17, at least one of the creation method of a finding remark or the criterion information may be displayed in association with each of the candidate finding remarks in the finding remark display area 43 of a display screen 40C corresponding to that in FIG. 9. In FIG. 17, "T2: NUMBER OF FINDING ITEMS 2" is displayed in association with a candidate 1 for the finding remark. Additionally, "NLP: LUNG, CANCER" is displayed in association with a candidate 2 for the finding remark. Further, "NLP" is displayed in association with a candidate 3 for the finding remark. T2 and NLP are examples of the creation method of a finding remark, and "NUMBER OF FINDING ITEMS 2" and "LUNG, CANCER" are examples of the criterion information.

Figure 18:
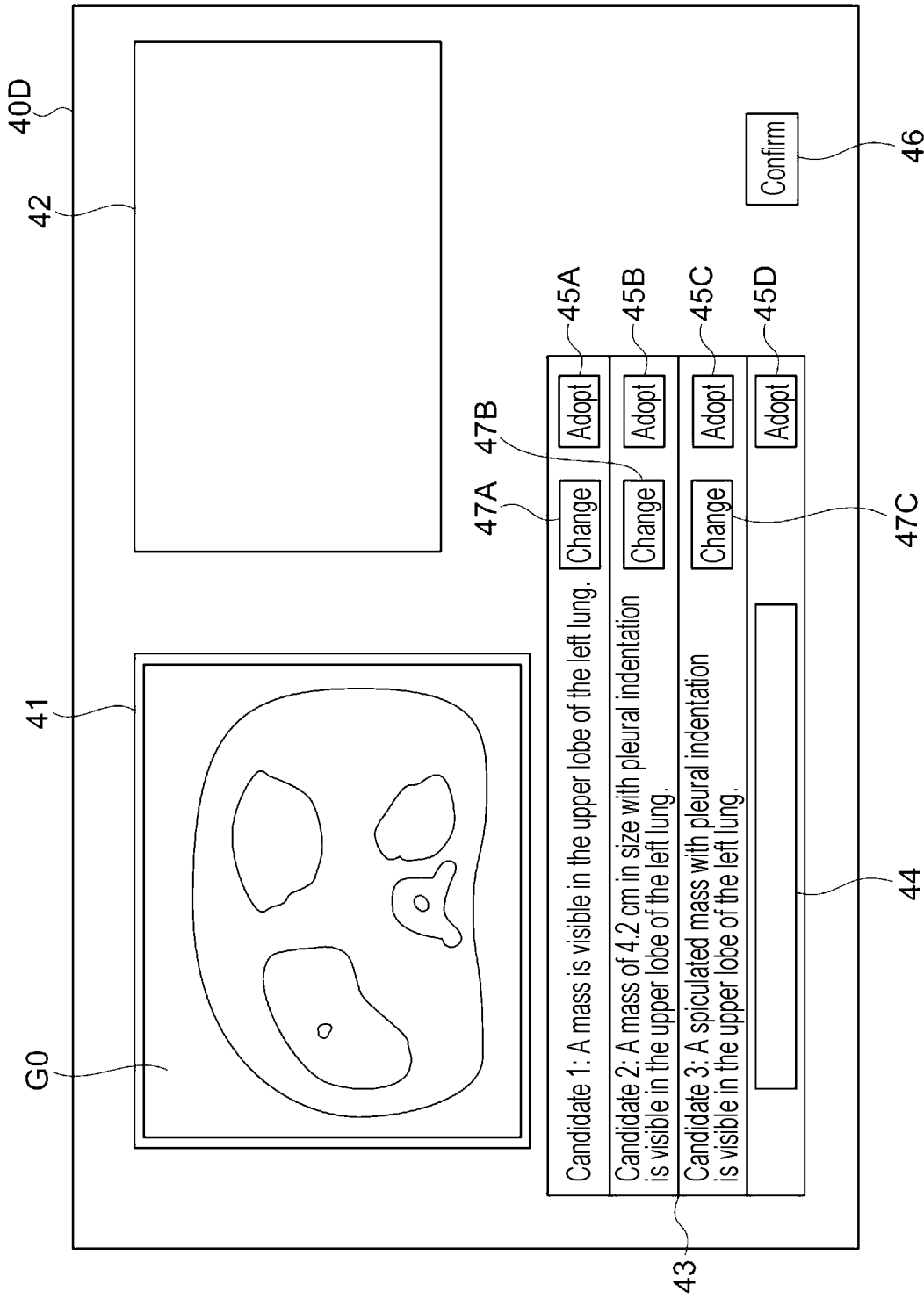
FIG. 18 is a diagram illustrating another example of the finding remark display screen.

Further, in each of the embodiments described above, the finding remark displayed in the finding remark display screen may be changed. For example, as illustrated in FIG. 18, change buttons 47A to 47C may be displayed in association with the respective candidate finding remarks in the finding remark display area 43 of a display screen 40D corresponding to that in FIG. 9, and the candidate finding remarks may be changed by selecting the change buttons 47A to 47C. In this case, for example, a candidate finding remark whose predicate is changed from "visible." to "suspected.", a candidate finding remark in which the finding used in the finding remark is changed, a candidate finding remark of which the creation method is changed, and the like are created as candidate finding remarks after the change in association with each of the candidates 1 to 3 with priority. In this case, in response to selection of one of the change buttons 47A to 47C, a correction start instruction for the selected candidate is accepted, and the display control unit 25 may display the candidate created for the selected candidate instead of the selected candidate in descending order of priority.

Figure 19:
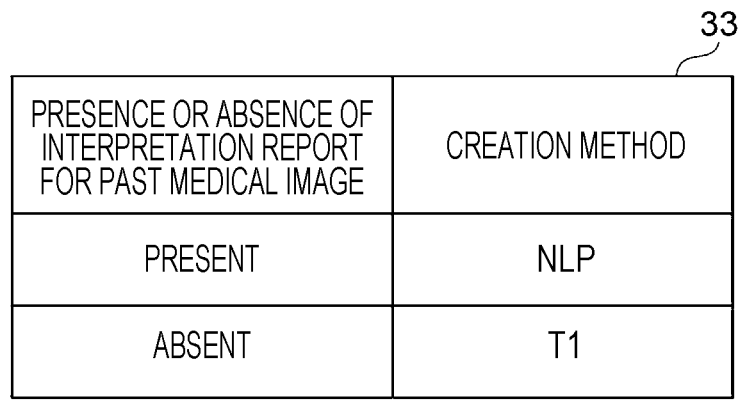
FIG. 19 is a diagram illustrating an example of a table in which the presence or absence of an interpretation report for a past medical image is associated with a document creation method.

In each of the embodiments described above, for the same patient as the patient for whom the medical image G0 has been acquired, a medical image of the same part may have been acquired and an interpretation report may have been created in the past. In such a case, the creation method determination unit 23 may determine the creation method of a document by using, as the criterion information, the presence or absence of an interpretation report created for the past medical image or the content of the interpretation report. In this case, the storage 13 stores a table 33 illustrated in FIG. 19. If an interpretation report for a past medical image has been created, the content of the interpretation report is preferably incorporated into an interpretation report newly created. Thus, the content to be written in the document to be created increases. Therefore, if an interpretation report for a past medical image has been created, the creation method of a document is determined to be NLP with reference to the table 33. On the other hand, if an interpretation report has not been created, the creation method of a document is determined to be the template T1. Note that if an interpretation report for a past medical image has been created, the document creation unit 24 may create a finding remark by using NLP and using a finding included in the interpretation report for the past medical image in addition to a finding included in the analysis result derived by the image analysis unit 22 for the medical image G0.

Figure 20:
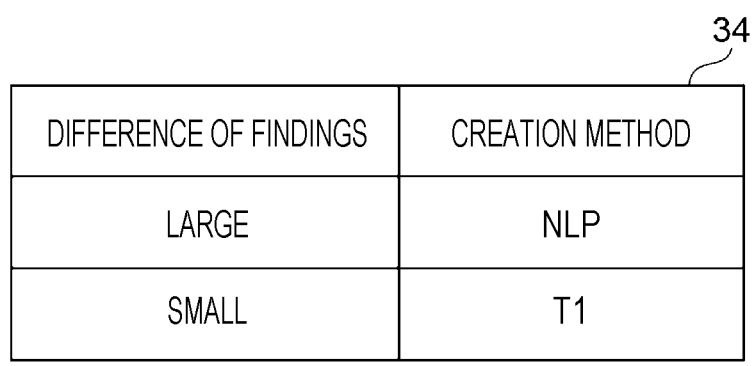
FIG. 20 is a diagram illustrating an example of a table in which whether a difference in findings is large or small is associated with a document creation method.

When the content of the interpretation report is used as the criterion information, the creation method determination unit 23 compares findings included in the analysis result derived by the image analysis unit 22 for the medical image G0 with findings included in the interpretation report for the past medical image. If a difference is large, the content to be written in the document to be created increases. Thus, the creation method of a document is determined to be the NLP. If the difference is small, the creation method of a document is determined to be the template. Note that the case where the difference is large includes, for example, a case where the difference in the finding regarding the size is greater than or equal to a predetermined threshold value, a case where a finding not included in the past interpretation report is included in the analysis result, or a case where a finding indicating the shape included in the past interpretation report is different from the finding included in the analysis result. In this case, the storage 13 may store a table 34 illustrated in FIG. 20, and the creation method may be determined in accordance with whether the difference between the findings is large or small with reference to the table 34.

Figure 21:
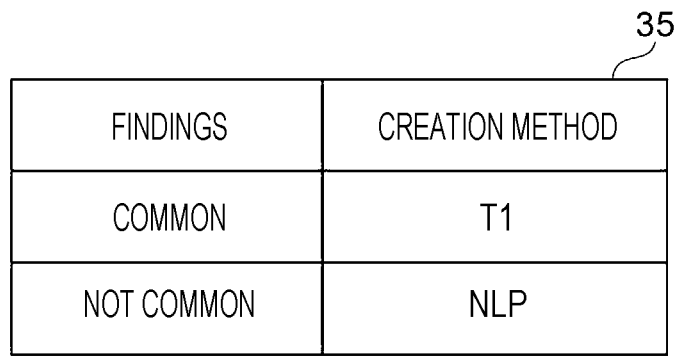
FIG. 21 is a diagram illustrating an example of a table in which the presence or absence of common findings is associated with a document creation method.

Additionally, when a patient is diagnosed, a plurality of types of medical images may be simultaneously acquired with different modalities. For example, a CT image and an MRI image may be acquired as medical images with both a CT apparatus and an MRI apparatus. In such a case, the creation method determination unit 23 may compare findings included in an analysis result of the CT image with findings included in an analysis result of the MRI image, and may determine the creation method of a document in accordance with the comparison result. For example, if the findings are not common, the content to be written in the document to be created increases. Thus, the creation method of a document is determined to be the NLP. If the findings are common, the content to be written in the document to be created is not so large. Thus, the creation method of a document is determined to be T1. In this case, the storage 13 may store a table 35 illustrated in FIG. 21, and the creation method may be determined depending on whether or not the findings for the CT image and the findings for the MRI image are common with reference to the table 35.

In each of the embodiments described above, the document creation apparatus 20 includes the image analysis unit 22, and analyzes the medical image G0 to acquire the analysis result. However, the configuration is not limited to this. The analysis result may be acquired based on an input by an operator using the input device 15.

In each of the embodiments described above, the process performed by the image analysis unit 22 of the document creation apparatus 20 may be performed by an external apparatus such as another analysis server connected to the network 10, for example. In this case, the external apparatus acquires the medical image G0 from the image server 5 and analyzes the medical image G0 to derive an analysis result. Then, the document creation apparatus 20 generates a finding remark by using the analysis result derived by the external apparatus.

In each of the embodiments described above, the technique of the present disclosure is applied to a case of generating a finding remark to be written in an interpretation report that is a medical document. However, the application is not limited to this. For example, the technique of the present disclosure may be applied to a case of creating medical documents other than an interpretation report, such as an electronic medical chart and a diagnostic report, and documents including a character string about other images.

In each of the embodiments described above, various kinds of processing are performed using the medical image G0 in which the diagnosis target is the lungs. However, the diagnosis target is not limited to the lungs. In addition to the lungs, any part of the human body such as the heart, the liver, the brain, and the limbs can be set as the diagnosis target.

In each of the embodiments described above, a document including the analysis result for the medical image G0 is created. However, the target image is not limited to the medical image G0. The present embodiments can be applied to a case where a photographic image is analyzed and a document including the analysis result is created in addition to the medical image G0.

Additionally, in the embodiments described above, various processors described below can be used as a hardware structure of a processing unit that executes various processes such as the image acquisition unit 21, the image analysis unit 22, the creation method determination unit 23, the document creation unit 24, the display control unit 25, and the document determination unit 26, for example. The aforementioned various processors include, in addition to a CPU which is a general-purpose processor that executes software (program) to function as the various processing units, a programmable logic device (PLD), such as a field programmable gate array (FPGA), which is a processor whose circuitry is changeable after production, a dedicated electric circuit, such as an application specific integrated circuit (ASIC), which is a processor having circuitry designed specifically for executing specific processing, and the like.

One processing unit may be constituted by one of these various processors, or by a combination of two or more processors of the same kind or different kinds (for example, a plurality of FPGAs or a combination of a CPU and an FPGA). In addition, a plurality of processing units may be constituted by a single processor. Examples in which the plurality of processing units are constituted by one processor include a first configuration, as exemplified by computers such as a server and a client, in which a combination of one or more CPUs and software constitutes one processor and this processor functions as the plurality of processing units. The examples also include a second configuration, as exemplified by a System On Chip (SoC) or the like, in which the processor that implements functions of the entire system including the plurality of processing units on a single integrated circuit (IC) chip is used. As described above, the various processing units are constituted using one or more of the various processors above in terms of the hardware structure.

Further, specifically, an electric circuit (circuitry) in which circuit elements such as semiconductor elements are combined can be used as a hardware structure of these various processors.

What is claimed is:

1. A document creation apparatus comprising:
   a memory that stores a plurality of creation methods comprising a plurality of templates and a plurality of trained models corresponding to different natural language processing schemes; and at least one processor configured to:
  perform image analysis on a medical image to acquire an analysis result including one or more findings;
  determine a number of the findings included in the analysis result so as to determine a creation method of a document to be created, wherein the number of the findings is associated with templates or natural language processing schemes;
  in response to the number of the findings being less than a predetermined threshold, determine that the creation method of the document to be created being one template corresponding to the number of findings among the plurality of templates, and create a finding remark by inserting the findings into the one template;
  in response to the number of findings being equal to or greater than the predetermined threshold, determine that the creation method of the document to be created being one natural language processing scheme corresponding to the number of findings among the plurality of natural language processing schemes, and create the finding remark by inputting the findings into the trained model among the plurality of trained models corresponding to the one natural language processing scheme; and
  create the document by using the created finding remark including a graphical display of the analysis result.

2. The document creation apparatus according to claim 1, wherein the at least one processor is configured to determine the creation method with reference to a table in which the number of the findings is associated with the creation method.

3. The document creation apparatus according to claim 1, wherein the at least one processor is configured to create a plurality of documents, and
  the plurality of documents are different in at least one of the finding or the creation method used in creation of the documents.

4. The document creation apparatus according to claim 3, wherein the at least one processor is configured to display the plurality of documents in a selectable manner.

5. The document creation apparatus according to claim 4, wherein the at least one processor is configured to display at least one of the creation method of each of the plurality of documents in association with the document.

6. The document creation apparatus according to claim 4, wherein the at least one processor is configured to:
  receive a correction start instruction for a document designated from among the plurality of documents that are displayed; and
  display, in response to the correction start instruction, another document that is different from the designated document in the creation method, instead of the designated document.

7. The document creation apparatus according to claim 1, wherein the document is a finding remark including the analysis result.

8. A document creation method comprising:
  storing a plurality of creation methods comprising a plurality of templates and a plurality of trained models corresponding to different natural language processing schemes in a memory;
  performing image analysis on a medical image to acquire an analysis result including one or more findings;
  determining a number of the findings included in the analysis result so as to determine a creation method of a document to be created, wherein the number of the findings is associated with templates or natural language processing schemes;
  in response to the number of the findings being less than a predetermined threshold, determining that the creation method of the document to be created being one template corresponding to the number of the findings among the plurality of templates, and creating a finding remark by inserting the findings into the one template;
  in response to the number of the findings being equal to or greater than the predetermined threshold, determining that the creation method of the document to be created being one natural language processing scheme, and creating the finding remark by inputting the findings into the trained model among the plurality of trained models corresponding to the one natural language processing scheme; and
  creating the document by using the created finding remark including a graphical display of the analysis result.

9. A non-transitory computer-readable storage medium that stores a document creation program for causing a computer to:
  store a plurality of creation methods comprising a plurality of templates and a plurality of trained models corresponding to different natural language processing schemes in a memory;
  perform image analysis on a medical image to acquire an analysis result including one or more findings;
  determine a number of the findings included in the analysis result so as to determine a creation method of a document to be created, wherein the number of the findings is associated with templates or natural language processing schemes;
  in response to the number of the findings being less than a predetermined threshold, determine that the creation method of the document to be created being one template corresponding to the number of findings among the plurality of templates, and create a finding remark by inserting the findings into the one template;
  in response to the number of the findings being equal to or greater than a predetermined threshold, determine that the creation method of the document to be created being one natural language processing scheme corresponding to the number of findings among the plurality of natural language processing schemes, and create the finding remark by inputting the findings into the trained model among the plurality of trained models corresponding to the one natural language processing scheme; and
  create the document by using the created finding remark including a graphical display of the analysis result.

* * * * *